(12) United States Patent
Dorawa et al.

(10) Patent No.: US 10,194,943 B2
(45) Date of Patent: Feb. 5, 2019

(54) ROD COUPLER WITH VARIABLE ANKLE POSITION

(75) Inventors: Klaus Dorawa, Schoenkirchen (DE); Axel Cremer, Fahrenkrug (DE); Adam Busch, Olten (CH); Manfred Müller, Bibern (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 112 days.

(21) Appl. No.: 14/344,078

(22) PCT Filed: Sep. 13, 2012

(86) PCT No.: PCT/EP2012/068012
§ 371 (c)(1),
(2), (4) Date: Dec. 11, 2014

(87) PCT Pub. No.: WO2013/037922
PCT Pub. Date: Mar. 21, 2013

(65) Prior Publication Data
US 2015/0133933 A1    May 14, 2015

(30) Foreign Application Priority Data
Sep. 15, 2011    (EP) .................................... 11181502

(51) Int. Cl.
*A61B 17/00*    (2006.01)
*A61B 17/60*    (2006.01)
(Continued)

(52) U.S. Cl.
CPC ............ *A61B 17/60* (2013.01); *A61B 17/645* (2013.01); *F16B 7/0426* (2013.01); *F16B 7/0486* (2013.01)

(58) Field of Classification Search
CPC ............................ A61B 17/60–17/666; A61B 17/7049–17/7052; F61B 7/0426; F61B 7/0486
See application file for complete search history.

(56) References Cited

U.S. PATENT DOCUMENTS 2,018,539 A * 10/1935 Welsh ....................... E04G 7/24
403/218
2,466,148 A *  4/1949 Birr ......................... A47C 7/004
248/188.7
(Continued)

OTHER PUBLICATIONS

Written Opinion International Search Report for PCT/EP2012/068012.

*Primary Examiner* — Jan Christopher Merene
*Assistant Examiner* — Steven Cotroneo
(74) *Attorney, Agent, or Firm* — Lerner, David, Littenberg, Krumholz & Mentlik, LLP

(57) ABSTRACT

The rod coupler according to the present invention comprises two clamping jaws and locking means for locking said clamping jaws against one another. Each clamping jaw comprises an outside surface and a clamping surface, the latter providing at least a first and a second groove. Each groove runs laterally from a different part of the outside surface extending into the rod coupler, wherein longitudinal axis of the first groove and the second groove include an angle that is equal to or less than 160 degrees. Opposing grooves form an aperture. The apertures are adapted for receiving a rod if the locking means is released. Clamping jaws that are locked by the locking means clamp the rods received in said apertures.

19 Claims, 4 Drawing Sheets

(51) Int. Cl.
*A61B 17/64* (2006.01)
*F16B 7/04* (2006.01)

(56) References Cited

U.S. PATENT DOCUMENTS

| | | | | |
|---|---|---|---|---|
| 2,658,776 | A * | 11/1953 | Wilcox | E04G 7/22 |
| | | | | 285/125.1 |
| 4,039,263 | A * | 8/1977 | Bassler | E04B 1/1906 |
| | | | | 403/171 |
| 4,347,690 | A * | 9/1982 | Wallace, Jr. | E04B 1/34326 |
| | | | | 135/160 |
| 4,529,331 | A * | 7/1985 | Schwartz | B63B 17/02 |
| | | | | 114/361 |
| 4,597,690 | A * | 7/1986 | Girard | F16B 7/04 |
| | | | | 403/312 |
| 4,747,569 | A * | 5/1988 | Hoshino | F16M 11/2021 |
| | | | | 248/291.1 |
| 4,869,147 | A * | 9/1989 | Hoshino | F16M 11/24 |
| | | | | 403/391 |
| 4,982,546 | A * | 1/1991 | Lange | E04B 1/1906 |
| | | | | 403/174 |
| 5,127,759 | A * | 7/1992 | Orbom | E04B 1/1903 |
| | | | | 403/171 |
| 5,342,361 | A * | 8/1994 | Yuan | A61B 17/7049 |
| | | | | 606/279 |
| 5,584,833 | A * | 12/1996 | Fournet-Fayard | A61B 17/7041 |
| | | | | 606/278 |
| 5,653,707 | A * | 8/1997 | Taylor | A61B 17/6416 |
| | | | | 606/54 |
| 5,702,394 | A * | 12/1997 | Henry | A61B 17/7049 |
| | | | | 606/265 |
| 5,728,096 | A * | 3/1998 | Faccioli | A61B 17/60 |
| | | | | 606/54 |
| 5,827,282 | A * | 10/1998 | Pennig | A61B 17/6458 |
| | | | | 606/54 |
| 6,032,430 | A * | 3/2000 | Soukup | E04B 1/585 |
| | | | | 403/170 |
| 6,102,911 | A * | 8/2000 | Faccioli | A61B 17/171 |
| | | | | 606/54 |
| 6,136,002 | A * | 10/2000 | Shih | A61B 17/7044 |
| | | | | 606/250 |
| 6,235,029 | B1 * | 5/2001 | Faccioli | A61B 17/66 |
| | | | | 606/54 |
| 6,273,633 | B1 * | 8/2001 | Husson | A47B 47/0016 |
| | | | | 403/171 |
| 6,409,729 | B1 * | 6/2002 | Martinelli | A61B 17/6466 |
| | | | | 606/59 |
| 8,469,944 | B2 * | 6/2013 | Mahlin | A61M 39/0247 |
| | | | | 604/533 |
| 8,998,961 | B1 * | 4/2015 | Ziemek | A61B 17/86 |
| | | | | 606/260 |
| 2006/0217710 | A1 | 9/2006 | Abdou | |
| 2006/0247629 | A1 * | 11/2006 | Maughan | A61B 17/6466 |
| | | | | 606/53 |
| 2007/0249979 | A1 | 10/2007 | Ara Pinilla et al. | |
| 2008/0226389 | A1 * | 9/2008 | James | F16B 7/0493 |
| | | | | 403/400 |
| 2009/0204153 | A1 * | 8/2009 | Suzuki | A61B 17/705 |
| | | | | 606/250 |
| 2010/0298827 | A1 * | 11/2010 | Cremer | A61B 17/6466 |
| | | | | 606/54 |
| 2011/0087226 | A1 | 4/2011 | Murner et al. | |
| 2013/0018421 | A1 * | 1/2013 | George | A61B 17/7044 |
| | | | | 606/278 |

* cited by examiner

ROD COUPLER WITH VARIABLE ANKLE POSITION

CROSS-REFERENCE TO RELATED APPLICATIONS

The present application is a national phase entry under 35 U.S.C. § 371 of International Application No. PCT/EP2012/068012 filed Sep. 13, 2012, published in English, which claims priority from European Patent Application No. 11181502.3, filed Sep. 15, 2011, all of which are hereby incorporated herein by reference.

TECHNICAL FIELD

The present invention relates to a rod coupler with a variable ankle position according to the preamble of claim 1.

PRIOR ART

External fixation frames are important tools e.g. for today's surgeons. In order to meet the specific need of an individual trauma situation, these frames are provided as modular systems. They typically include e.g. multiple rods and rod interconnecting devices like couplers. Said rods extend e.g. longitudinally of a limp or other body parts. By means of the couplers, said rods can be assembled into external fixation frames of desired design, wherein the frame is then e.g. adapted to carry pins, plates, rings or the like that engage with traumatized body parts. Multi-functional rod couplers allow for a secure connection of rods in a large variety of frame configurations. Thereby it is possible to accommodate different spatial relations between the said pins, plates, or rings in order to e.g. stabilize the trauma region.

An external skeletal fixation system is taught in the U.S. Pat. No. 5,653,707. This fixation system comprises bars with a hexagonal cross section and a connector for interconnecting said bars. The connector comprises hexagonal apertures, corresponding substantially with said bar cross section, in which the bar can be received. Such hexagonal cross sections do, however, set restrictions on the axial alignment of said bars. Further, the connector guides the interconnected bars such that they do pass one another side-by-side, i.e. the connected bars do not lie in a common plane (except for the trivial case when the bars are parallel). Further, the angle between longitudinal axes of received bars is secured only by a force fit. Hence, this construction is not suitable when the frame has to withstand large forces, e.g. when the frame has to bridge long distances.

An external wrist fixator is described in the US Patent Application No. 2007/0249979 A1. Said fixator consists of two bars and a main articulator with two identical pitches at a lateral distance to one another, whereon spherical bearings are positioned. Each of the two bars engages into one spherical bearing. A tightening screw transversely mounted on the articulator makes it possible to tighten the spherical bearings and thus fixing or clamping the bars. Hence the bars are fixable in a variety of configurations. This technical solution does, however, not provide enough stability for heavily stressed fixator frames as the spherical bearings are kept in a force fit only and tend to slip in the pitches. Moreover, this teaching is not suited for securely fixing the bars in a common plane, in particular when a large angle between the longitudinal axes of the bars is required.

SUMMARY OF THE INVENTION

It is an object of the present invention to provide a rod coupler for coupling rods which provides enhanced stability. It is a further object, to provide a cost-efficient device. These objects are achieved by a rod coupler having the features of claim 1.

Advantageous embodiments of the invention, overcoming the above mentioned disadvantages, are laid down in the dependent claims.

The objects of the present invention is achieved by a rod coupler comprising a first clamping jaw, a second clamping jaw, and locking means for locking said clamping jaws against one another, wherein each clamping jaw comprises an outside surface and a clamping surface, wherein each clamping surface provides at least two straight grooves, each groove running laterally from a different part of the outside surface extending into the rod coupler, wherein longitudinal axes of a first groove and a second groove of said grooves on one clamping surface include an angle that is equal to or less than 160 degrees, wherein said grooves are positioned on the clamping surfaces such that, when the clamping jaws face one another with their clamping surfaces in locking position, at least the first and the second groove of the at least two grooves of the first clamping jaw face each a groove of the second clamping jaw, wherein opposing grooves form an aperture, wherein each of the at least two apertures extends laterally from the outside surface of said clamping jaws into the rod coupler and is adapted for receiving a rod when the locking means is released, and in that the clamping jaws locked by the locking means clamp the rods received in said apertures.

Here, the term "opposing" and related terms have to be understood as "being provided on different clamping jaws that face one another".

Said angle may be smaller than or equal to an angle of about 150 degrees, 140 degrees, 130 degrees, 120 degrees, or 100 or 90 degrees, being preferably in a range from 120 degrees to 160 degrees.

The apertures are substantially cylindrical recesses, each extending with its cylindrical axis substantially parallel to the opposing clamping surfaces of clamped clamping jaws.

In a preferred embodiment, the rod coupler consists of two opposing clamping jaws and locking means for locking said clamping jaws against one another, the locking means being preferably one or two screws with nuts. In a particularly preferred embodiment the rod coupler consist of two identical clamping jaws and locking means for locking them together. Identical clamping jaws, i.e. structurally identical pieces, lower on the one hand the production costs and on the other hand the error risk during assembling the device.

Preferably, said clamped rods are positively locked at least with respect to said angle.

The rods can be coupled in a V-shape configuration with said angle as the angle defined by the V-shape.

The rod coupler has preferably at least one of said at least two apertures provided as a through-aperture through the rod coupler, extending laterally from one part of said outside surface to another part and adapted to each clamp the rod received and pushed through said through-aperture.

The through-apertures allow building of Y-constructions in that one of the rods can be pushed past the other(s) to exit the rod coupler on the other side. Hence the rod coupler can be shifted along one guiding rod while the other rod(s) remains in unchanged relative position to the rod coupler. Thus the ankle position, i.e. the position where the guiding and the coupled rods come closest, can be adjusted to the present needs.

In order to allow multi-functionality of the rod coupler, all apertures may be provided as through-apertures through the rod coupler, extending laterally from one part of said outside surface to another part and adapted to receive and clamp one rod pushed through said through-aperture. This is, however, not necessary.

Further it is possible to provide at least two of the at least two apertures as merging into one another. When at least one of the two merging apertures is provided as a through-aperture then a crossing point is given where the two apertures cross.

Preferably, the aperture-forming grooves extend each so close to a lateral edge (i.e. a side) of the clamping jaw that a residual edge-site part of the clamping jaw, i.e. a part that is outwardly of the clamping jaw with respect to the groove, defines or limits the groove laterally such that opposing grooves form a preferably substantially convex aperture that allows accommodation of a rod, the latter being securely encompassed by the aperture. Preferably, the lateral edges are sides of the clamping jaws that constitute sides of the rod coupler, wherein said sides or edges form an angle with respect to one another that is substantially equal or larger than said angle between the longitudinal axes of said grooves.

It is further preferred that the grooves are extending through the entire clamping jaw and therefore cut out portions of said residual edge-site part, i.e. the outer groove wall. This means, in particular, that, at one end of the groove, the groove cuts out a portion of the outer wall of the crossed groove. The two opposing cut-out portions of said edge-site part or outer groove wall form the openings of the apertures. Having the crossing point of the grooves close to the edge of the clamping jaw, i.e. close to the crossing point of the edges of the clamping jaw, brings said cut-out portions close together (centimeter or millimeter range). The portion of the outer groove wall that remains between the neighboring cut-out portions on the same clamping jaw forms a protrusion or a corner that extends in a direction substantially perpendicular to the longitudinal direction of the groove. Said corner therefore extends from the crossing point of the grooves in a direction substantially perpendicular to the opposing jaw surfaces and defines with an inner surface an end portion of the groove or the groove wall. A rod that is received in the groove (or an aperture) is supported by said corner, more specifically by the corner's inner surface. Consequently, this corner provides additional clamping stability.

For clamping or locking the two clamping jaws against one another, a locking means is provided. Screws are the preferred means for locking the jaws, but alternatively also quick-acting clamps or clamping means using an eccentric element, or other locking means known to a person skilled in the art may be used. In the case that screws comprising a screw head, a screw pin, and a thread are used, the clamping jaws preferably provide in locking position at least one through-hole that runs straightly from the outside surface of the first clamping jaw through the opposing clamping surfaces to the outside surface of the second clamping jaw. At least one screw is then provided to be received in the at least one through-hole, and preferably locked in clockwise rotation, for locking the clamping jaws. For tightening the screw, a nut can be provided as a counter-part, wherein the clamping jaws are locked between a screw head and said nut. Alternatively, an internal thread can be formed into said through-holes suited for mating with the screw thread. Partially threaded screws are preferred since they help to avoid screw loosening while the clamping jaws are open. When the through-holes provide an internal thread, it is beneficial to have a screw pin with a smaller diameter than the screw thread diameter. This ensures that, if the two clamping jaws are identical clamping jaws, the screw can be guided through one clamping jaw in order to engage into the internal thread provided by the following clamping jaw.

Particularly preferred are clamping jaws that provide in locking position at least two or more vertical through-holes that run straightly from the outside surface of the first clamping jaw, through the opposing clamping surfaces, to the outside surface of the second clamping jaw, wherein said locking means comprises screws, one of them received in each through-hole for locking the clamping jaws.

Further, it is preferred that each clamping jaw provides a protrusion or a projection on its clamping surface, wherein said protrusions provide each a lateral protrusion surface, wherein the lateral protrusion surfaces of said clamping jaws act together as a stop against further relative rotation, preferably clockwise rotation, when said clamping jaws are in locking position.

A further example of the rod coupler according to invention is characterized in that each of said clamping jaws provides three or four or more straight grooves on its clamping surface. Said grooves are then provided with their longitudinal axes at different angles with respect to one another and forming three or four or more apertures for receiving three or four or more rods when said clamping jaws are in locking position. Thereby, three, four or more rods can be coupled together, wherein a part or all of the receiving apertures may be through-apertures or not, and wherein individual apertures may cross one another or not.

Also, each clamping jaw comprises preferably at least one further recess from the outside surface to the clamping surface, wherein said at least one further recesses preferably form a through-opening through the rod coupler when the clamping jaws are in locking position. This helps to reduce weight and to safe material. These recesses may further provide hand gripping portions, which facilities the handling of the coupling device. Hence, these recesses, not intended for use by the locking means, are preferably sized large enough for allowing the user to reach in or through such a recess with at least one, preferably at least two fingers for a safe grip.

A particularly preferred embodiment consists of two identical clamping jaws and two screws with nuts as locking means. Each clamping jaw provides two straight grooves running substantially parallel to a first and a second outer edge or side of the clamping jaw and toward one another under a predefined angle. The grooves cross one another in the crossing point. One side of said recess is extending substantially parallel to a third outer edge of the same clamping jaw, said third outer edge opposing said first and second edge. The recess is preferably tapered in the direction perpendicular to the third edge and parallel to the clamping surface and extends, in this very direction, preferably substantially up to the crossing point of the grooves. The recess may cut over a distance of $\frac{1}{10}$ to $\frac{1}{3}$ of the groove width laterally into the grooves so that the clamped rods are visible through the recess once inserted into the rod coupler. Preferably, the recess has a substantially triangular shape. The outer edges of the clamping jaw, except the ones defining the limit of or being provided on the clamping surface, are beveled in the direction of the screw holes, i.e. in the direction substantially perpendicular to the clamping surface; hence the rod coupler exhibits a generally convex shape. The holes for the two screws are located on either side of the recess, in direction of said third edge of the recess, i.e. on or close (1 to 10 millimeter range) to the extended hypotenuse. Screw heads and nuts project over the outer surfaces of the clamping jaw, thereby being easily accessible. In another embodiment, the screw heads and/or the nuts may be at least partially or completely countersunk.

The rod coupler may vary considerably in design (e.g. number of apertures or angles between the individual apertures) and capabilities (e.g. number of through-apertures for receiving rods), and may include materials including metals, alloys, plastics, composites, and ceramics.

Preferably, the two clamping jaws are of identical shape or design and, moreover, the clamping jaws are preferably provided as a single piece. This reduces production costs and facilitates the assembling of the fixation frame, as the risk of mixing-up said clamping jaws is removed. A typical fixation frame comprises a plurality of rods and rod couplers. But also a construction consisting out of two rods and a single rod coupler is considered as a frame. These frames may be used in the field of medicine, e.g. by surgeons, or where there is a need for coupling rods or bars in general.

It is, however, possible, that one of the clamping jaws provides additional grooves, e.g. that one jaw provides three grooves, while the other provides only two or that opposing grooves, i.e. grooves from different clamping jaws, exhibit different shapes. It is even possible that only one clamping jaw provides grooves, wherein the opposing clamping jaw provides a substantially flat clamping surface. In the case that rods of the same cross section have to be coupled, the grooves on the same clamping surface may have the same shape, or even length. It is to be understood, that the rod coupler may also provide differently-shaped grooves on the same clamping surface, wherein opposing grooves then may have the same cross section. In this case, the apertures formed by the grooves may have a different cross section for coupling differently-shaped rods, e.g. a rod and a thinner rod, or a rod with a rectangular cross section and a circular-cylindrically-shaped rod.

Further, it may be that one aperture is deeper or longer than the other one, i.e. the length of the respective grooves are not the same. A deeper aperture provides naturally more contact surface with the received rod, hence a better clamping effect. Such an asymmetric rod coupler may be used, when rods of substantially different lengths have to be coupled. The longer rod, which is expected to exert more stress on the coupler, would then be advantageously received in the longer or deeper aperture.

It is to be understood that the rod coupler can couple or interconnect rods, bars, pins, or more generally substantially cylindrically-shaped or lengthy objects of a corresponding diameter.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
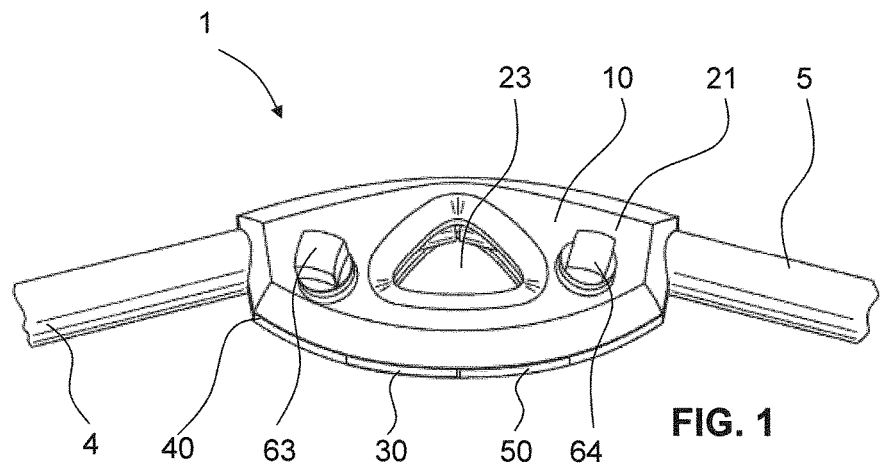
FIG. 1 shows a top view of an embodiment of the rod coupler with two coupled rods clamped between two clamping jaws.
Figure 2:
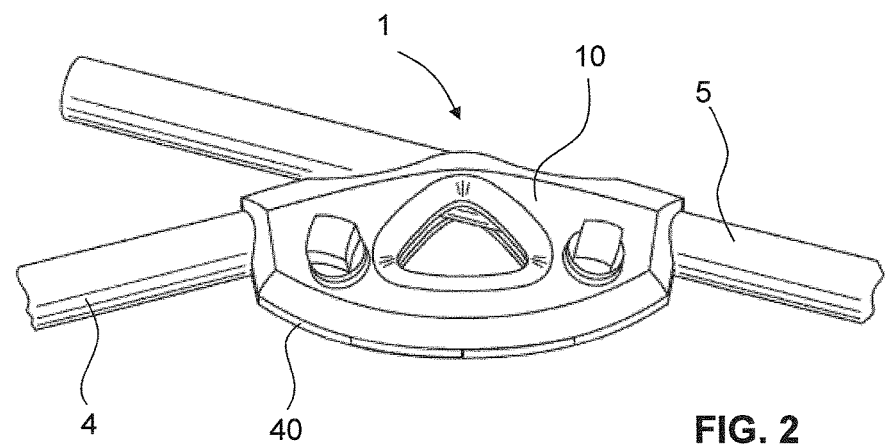
FIG. 2 shows a top view of the rod coupler according to FIG. 1, wherein one rod is pushed past the other rod.

A preferred embodiment of an assembled and locked rod coupler 1 is shown in FIGS. 1, 2, 7, and 8. In said figures, the rod coupler 1 couples two individual rods, e.g. for creating an external fixation frame to be used by e.g. a surgeon. The rod coupler 1 is typically 5 to 15 centimeters long, 2 to 10 centimeters wide and 1 to 3 centimeters high. It comprises preferably two identical clamping members or clamping jaws 10, 40 that correspond with and engaged into one another in locking position. Further, two screws 63, 64 for locking said clamping jaws 10, 40 against one another in locking position are provided. The screws 63, 64 comprise each a screw head 65, 66, a screw bolt or pin 67, 68, and a thread 69, 70. The diameter of the bolt portion connecting the head 65, 66 and the threaded portion 69, 70 is smaller than the diameter of the threaded portion 69, 70. This ensures that the screw 63, 64 can be guided through the first into the second clamping jaw 10, 40.

The clamping jaws 10, 40 are each provided as identical semi-shells that fit into one another. Said clamping jaws 10, 40 are preferably produced from a single piece. They comprise an outside surface 21, 41 that merges in an edge region with a clamping surface 22, 42.

In the lateral edge region, at its outer end, the clamping jaw 10, 40 is limited by two laterally opposing long sides 6, 8. Said long sides 6, 8 are connected by two laterally opposing narrow sides 7 (cf. FIG. 1). One of said long sides 6, 8 is a convexly curved side 6 the other one is provided in two substantially straightly running long side portions 8. Each of said long side portions 8 extends in horizontal direction straightly and under the same angle from one respective narrow side 7, wherein said portions 8 merge on half way and form a with respect to the rod coupler 1 laterally outwardly pointing corner 9. Further, the lateral end regions of the outside surface 21, 41 are beveled, at least in the lateral end region, such that the outside surfaces 21, 41 of clamping jaws 10, 40 in locking position approach one another toward said narrow sides 7 and long sides 6, 8. The edges, where the outside surface 21, 41 and the respective clamping surface 22, 42 merge, including corner 9, are preferably flattened. This reduces the risk of injury while handling the coupler 1.

Figure 3:
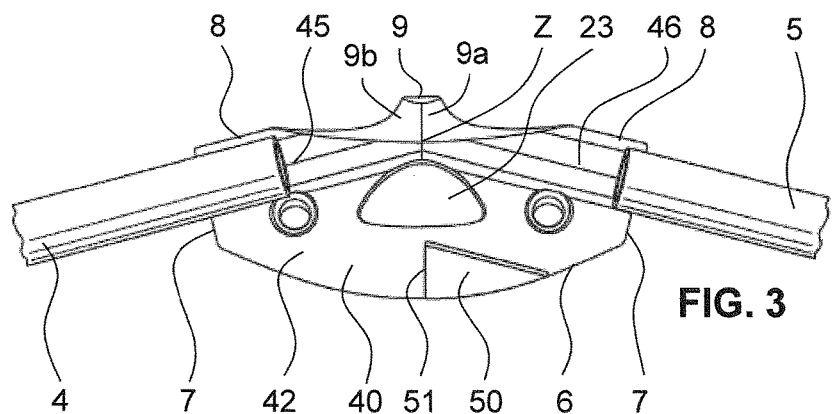
FIG. 3 shows a part of the rod coupler according to FIG. 1, i.e. one clamping jaw is removed.
Figure 4:
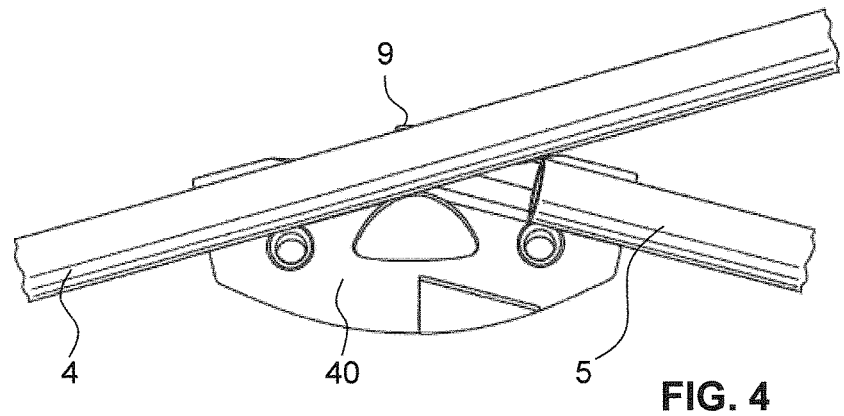
FIG. 4 shows a part of the rod coupler according to FIG. 1, i.e. one clamping jaw is removed, wherein one rod is pushed past the other rod.
Figure 5:
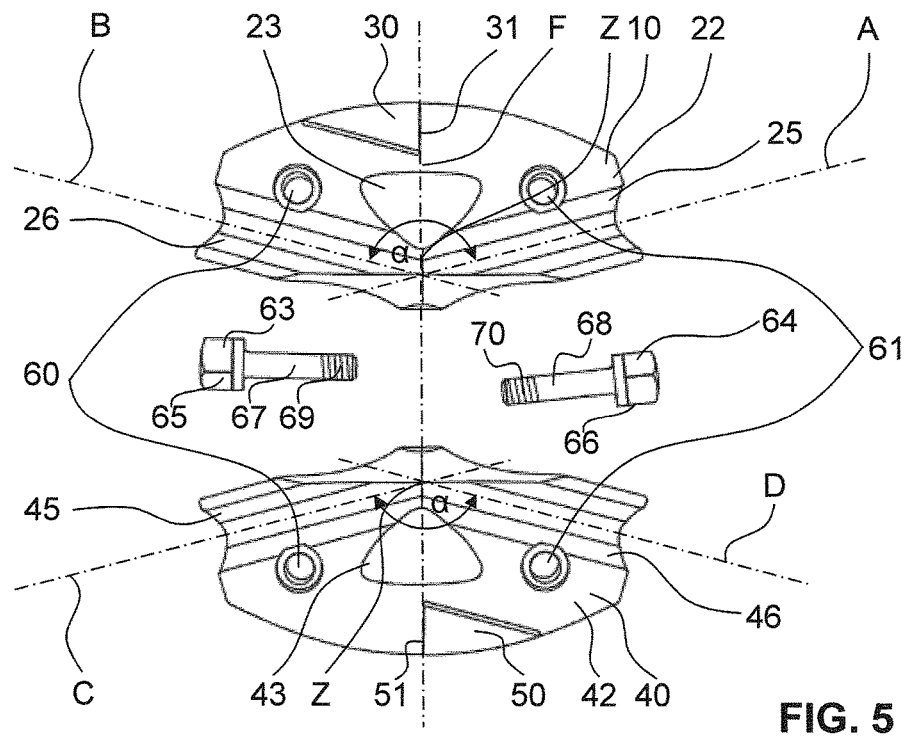
FIG. 5 shows the disassembled rod coupler according to claim 1.
Figure 6:
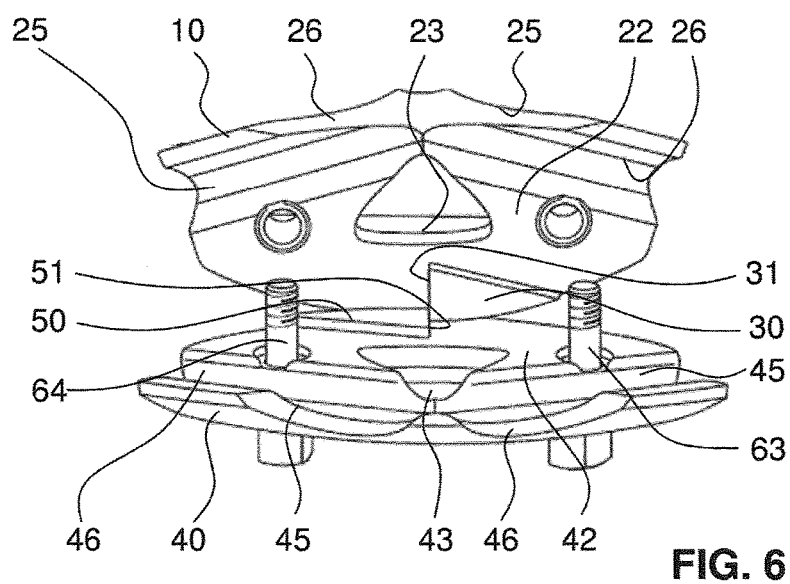
FIG. 6 shows an open rod coupler according to claim 1.

Corners or corner pieces 9 are formed, if grooves 25, 26, 45, 46 cross one another in a crossing point Z on the clamping surface 22, 42 and extend from Z toward the outside surface 21, 41. From FIG. 3 it is obvious that corner 9 is a consequence of the crossing point Z being close to the lateral edge of the clamping jaw 10, 40 and of the crossing groove 25, 45 or 26, 46 cutting through the long side portion 8 of the groove 26, 46, or 25, 45; i.e. a lateral edge part or outer wall part of the groove 26, 46, or 25, 45 is cut through by the crossing groove 25, 45 or 26, 46. Corners 9 are thus part of a projecting wall part close to long side portion 8 that defines the groove 26, 46, or 25, 45 laterally. Corners 9 protrude from the crossing point Z substantially perpendicularly to the clamping surface 22, 42 such that the rod 4, 5, the latter being received in a respective groove 25, 26, 45, 46 and being positioned such that it extends over crossing point Z and at least to the corner 9, contacts an inner surface 9a, 9b of said corner 9 (cf. FIG. 3). From FIG. 3 can be seen that the inner surfaces 9a and 9b of corner of clamping jaw 40 are defining parts of groove 45 and groove 46, respectively. The same applies for the respective corner 9 of clamping jaw 30 with grooves 25, 26. The corners 9 of the two clamping jaws 10, 40 in clamping position extend towards one another (cf. FIG. 8). From FIG. 4, it is obvious that the pushed-through rod 4 contacts the inner surface 9a (not visible in FIG. 4, cf. FIG. 3) and provides further support guidance to rod 4. The supporting and guiding function of corners 9 allow for a compact and stable construction of the rod coupler 1.

FIGS. 3 to 6 show the rod coupler 1 in different views and disassembled states. From these figures is apparent that each clamping surface 22, 42 provides a first groove 25, 45 with a longitudinal axis A, C and a second groove 26, 46 with a longitudinal axis B, D (cf. in particular FIG. 5).

In this embodiment, an angle α between the longitudinal axes A and B and between the longitudinal axes C and D is about 150 degrees. The angle α is the angle between the entry points of the rods 4, 5 on the long curved side 6 and the crossing point Z of the grooves 25, 26, 45, 46 (cf. FIG. 5). Other embodiments may provide apertures 55, 56 that do not cross one another or that are not through-apertures, hence the crossing point Z may be a hypothetical crossing point between longitudinal axes outside the rod coupler. In other embodiments the angle α ranges between 0 degrees and 160 degrees, in particular between 10 and 150 degrees or between 20 and 130 degrees or 140 degrees.

Here, the first groove 25, 45 extends from one narrow side 7 and runs parallel to the respective long side portion 8 of the clamping jaw 10, 40, passes the corner 9 and cuts the outside surface 21, 41. The second groove 26, 46 extends from the other narrow side 7 and runs parallel to the other long side portion 8, passes the corner 9 and cuts the outside surface 21, 41 (cf. FIG. 8). Further, on each clamping surface 22, 42, the first and second grooves 25, 45, 26, 46 cross one another in a crossing point Z. The grooves 25, 26, 45, 46 have in this embodiment identical diameters of 0.5 to 2 centimeter, a depth that is preferably equal to or less than their width, and they run preferably with their outer edge, i.e. the edge that is parallel to the longitudinal axis and closer to the respective long side portion 8, at a lateral distance to the respective edge of the long side portion 8 of about 0.2 to 1.5 centimeter. A cross section of the grooves 25, 26, 45, 46 is preferably of part circular shape, i.e. the depth of the groove is equal to or smaller than half of its diameter or width. In other embodiments, also elliptical or polygonal shapes are possible. Preferably, the cross section of the grooves 25, 26, 45, 46 corresponds to the part of a cross section of the rod 4, 5 that it contacts during clamping. An elliptically-shaped groove, or in general a groove that has a width that is larger than its depth, allows for clamping rods 4, 5, in particular of circular-cylindrical shape, of different diameters.

Alternatively, the clamping jaws 10, 40 may provide different grooves 25, 26, 45, 46 to form different apertures 55, 56 that have different diameters or shapes for clamping rods 4, 5 of preferably accordingly different diameters or shapes. Here, it is preferred that opposing grooves 25, 26, 45, 46 from different clamping jaws 10, 40 are mirror images of one another with respect to a plane substantially parallel to the clamping surfaces 22, 42. In this case, the longitudinal axes of the apertures 55, 56 lie preferably but not necessarily in a plane substantially parallel to the clamping surfaces 22, 42. It may, however, also be beneficial to have different opposing groove shapes that complete one another to form an aperture cross section that corresponds to the cross section of the respective rod 4, 5 to be clamped.

The groove pattern, i.e. the arrangement of grooves, here the first and second grooves 25, 26, 45, 46 on the clamping surfaces 22, 42 are mirror images of one another with respect to a mirror plane parallel to the clamping surface 22, 42. There is a further mirror plane in respect of the first and second grooves 25, 26, 45, 46 that is perpendicular to the previously mentioned mirror plane and runs through a symmetry axis F; said mirror axis F runs horizontally between the two screws 63, 64, through corner 9, and substantially parallel to the respective clamping surface 22, 42 (cf. FIG. 5). Hence, when the two identical clamping jaws 10, 40 are in locking position, i.e. when the clamping jaws 10, 40 face one another with their clamping surfaces 22, 42, apertures 55, 56 are formed by opposing grooves 25, 46, 26, 45 from different clamping jaws 10, 40

The apertures 55, 56 are horizontally running, i.e. substantially parallel to the clamping surface 22, 42 extending, and substantially cylindrically shaped through-apertures or through-openings through the rod coupler 1. They extend from the narrow side 7 parallel along the nearest neighboring long side portion 8 and cut through the opposing long side portion 8. The longitudinal direction of the apertures 55, 56 extends thus from the narrow side 7 to the long side portion 8 that is opposite to said narrow side 7. The through-apertures 55, 56 extend in a lateral direction (their width) from the outer wall provided on the side of the substantially parallel running long side portion 8 toward the middle of the rod coupler 1, where the recess 23, 43 and screw holes 60, 61 are provided. Said apertures 55, 56 are adapted for receiving rods 4, 5 with a diameter that is equal to or larger than twice the depth of the grooves 25, 26, 45, 46 that form said apertures 55, 56. The rods 4, 5 received in apertures 55 and 56 lie in a common plane that is substantially parallel to the plane that is span by the clamping surfaces 22, 42.

Here, both rods 4, 5 can be pushed into the apertures 55, 56 until the respective ends of the rods 4, 5 lie at short distance before the crossing point Z. The two rods 4, 5 are arranged in a V-shaped configuration and include the angle α. One of both can then also be pushed further into the respective aperture 55, 56 to pass the other rod and the crossing point Z, and, if required, to exit the rod coupler 1 on the opposing long side portion 8 (cf. FIG. 2). With one rod 4, 5 passing the other rod and the crossing point Z, instead of the V-shaped construction (cf. FIG. 1) a Y-shaped construction (cf. FIG. 2), with the rods 4, 5 lying in a single, common plane, can be realized. By means of this push-through function, it is possible to adapt the bridging length of the rods and also the ankle position, which helps to optimize the bridging frame to the present trauma situation.

Through-apertures 55, 56 offer the additional advantage that rods 4, 5 can be inserted from both sides. Further, even two rods 4, 5 may be inserted into on single through-aperture 55, 56, through opposing openings of the through-aperture 55, 66; said rods 4, 5 may subsequently be clamped, and thereby coupled together.

In another embodiment, said apertures 55, 56 may end in the rod coupler 1, i.e. they are not through-apertures. Here, the push-through function is not available. This embodiment is advantageous in the sense that it allows for a defined insertion depth of the rods 4, 5, hence making possible a quick and safe assembly of fixation or bridging frames.

In order to clamp in apertures 55, 56 received rods 4, 5, the two clamping jaws 10, 40 provide two through-holes 60, 61. These holes 60, 61 are located away, i.e. at distance, to said grooves 25, 26, 45, 46 in order to not block the insertion or rods 4, 5. When the clamping jaws 10, 40 are in locking position, said holes 60, 61 extend from the outside surface 21, 41 of one clamping jaw 10, 40, through both clamping surfaces 22, 42, to the outside surface 41, 21 of the opposing clamping jaw 40, 10. Two screws 63, 64, preferably with nuts 71, 72 (cf. FIG. 7), are provided that can be received in said through-holes 60, 61 and tightened in the corresponding nuts, preferably in clockwise rotation. Upon tightening a screw head and a corresponding nut the force is guided in know manner to press the clamping jaws 10, 40 together in order to clamp rods 4, 5 received in the apertures 55, 56. In another embodiment, a single or three or more through-holes and screws may be provided.

Figure 7:
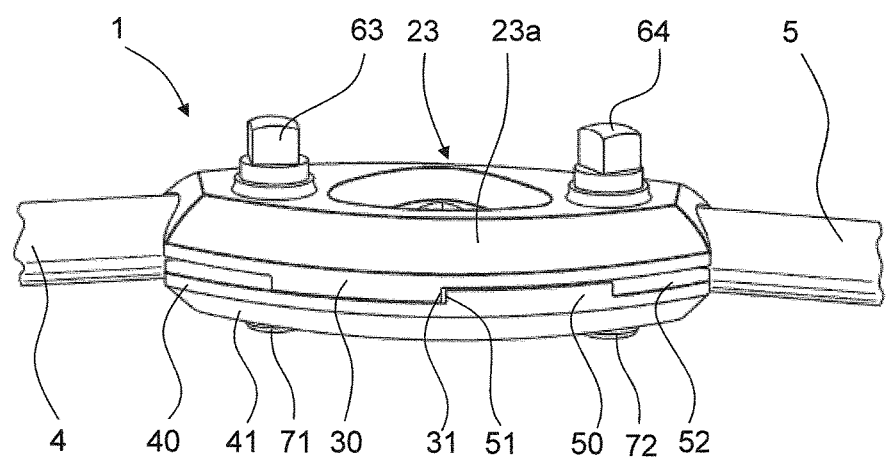
FIG. 7 shows a rear view of the rod coupler according to FIG. 1.
Figure 8:
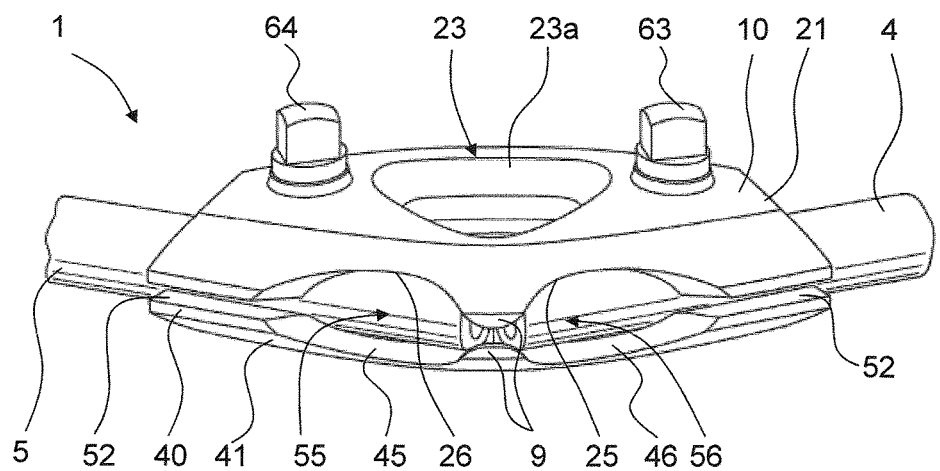
FIG. 8 shows a front view of the rod coupler according to FIG. 1.

In the case that the vertical diameter of the received rod 4, 5 is substantially larger than the sum of the depth of the opposing grooves 25, 26, 45, 46 that form the rod-receiving aperture 55, 56, there might be a gap 52 between the clamping jaws (cf. FIG. 7).

In order to help the user finding the proper locking position of the two clamping jaws 10, 40 and in order to facilitate the tightening of the screws 63, 64, each clamping surface 22, 42 provides a protrusion 30, 50. Said protrusion 30, 50 is preferably (but not necessarily) located between the two grooves 25, 26, 45, 46 and the convexly curved long side 6, on the right side of the middle axis F in direction from the long side 6 to the corner 9. Preferably, the protrusion 30, 50 is of a substantially triangular shape (cf. FIGS. 3 to 6), has a 0.5 to 4 centimeter long convexly curved side surface common with the long side 6, and a step height of 1 to 3 millimeter. The protrusion may just fill said gap 52 (cf. FIG. 7). The protrusion 30, 50 further provides a lateral protrusion surface 31, 51 that is located in a vertical plane through the middle axis F. These lateral protrusion surfaces 31, 51 contact one another over their length of 0.5 to 2 centimeter, preferably 1 centimeter, when the clamping jaws 10, 40 are in locking position. Thereby, a stop is provided that helps to find the locking position and facilitates the tightening of the screws 63, 64. Further, the contact between the stop surfaces or lateral protrusion surfaces 31, 51 is enforced while tightening the screws in clockwise rotation. Alternatively (not shown in the drawings), the protrusion 30, 50 can be provided on the other side of said symmetry axis F. In this case, it is, however, advantageous to have screws with a counter-clockwise oriented thread for ensuring a good contact between the lateral protrusion surfaces 31, 51. It should be noted that the protrusion 30, 50 breaks the internal mirror symmetry of the respective clamping jaw 10, 40 in relation to the previously mentioned mirror planes. While such protrusions 30, 50 are preferable in practical terms, they are not absolutely necessary.

In order to make the rod coupler 1 lighter, a recess 23, 43 is provided, extending from the middle region of the outside surface 21, 41 vertically to the respective clamping surface 22, 42. Preferably, said recess 23, 43 exhibits, in top view, a triangular shape with smoothed corners and tapered edges. The legs of the triangle, i.e. the first and second sides of recess 23, 43, extend substantially into the direction of the respective closest neighboring groove 25, 26, 45, 46, whereas the hypotenuse extends substantially perpendicular to the angle bisecting line between the longitudinal axes A, B or C, D. The portion 23a of each clamping jaw 10, 40 extends along the hypotenuse of said triangle and serves as gripping portion for a user. The portion 23a of each clamping jaw 10, 40 provides a single gripping portion; if the clamping jaws 10, 40 are in clamped configuration, the two individual portions 23a form a single gripping portion. The user may insert one or more fingers into said recess 23, 43 for a better grip while handling the rod coupler 1 or while assembling it. Once the two clamping jaws 10, 40 are arranged in locking position, the recesses 23, 43 of both clamping jaws 10, 40 overlap and form a through-opening through the rod coupler 1, from the outside surface 21, 41 of one clamping jaw 10, 40 to the outside surface 41, of the other clamping jaw 40, 10. One side of the triangular-shaped recess 23, 43 of the clamping jaw 10, 40 is substantially parallel to the long curved side 6 of the respective clamping jaw 10, 40. The opposing vertex of the triangle points toward corner 9.

Said recess 23, 43 may cut the grooves 25, 26, 45, 46 in the area of said vertex for making visible the rods 4, 5 in the assembled rod coupler 1 from the outside (cf. FIGS. 1 to 6).

The simple rod coupler 1 can be produced cost-efficiently and allows to couple rods 4, 5 preferably in a Y-shaped or at least in a V-shaped configuration, wherein the rods 4, 5 lie in a common plane. The ankle position is easily shiftable and the bridging length of the rods 4, 5 is easily adaptable, in particular by changing the insertion depth of the rods 4, 5 into the apertures 55, 56 or by the push-through function. All this may be beneficial for creating complex frames. Furthermore, usage of identical clamping jaws 10, 40 lowers productions costs and also the risk of errors during assembling of the fixation frame. Also, the present rod coupler allows for a quick, easy, and safe assembling of a fixation frame that is adapted to the present needs.

| LIST OF REFERENCE SIGNS | |
|---|---|
| 1 | Rod coupler |
| 4 | First rod |
| 5 | Second rod |
| 6 | Long curved side |
| 7 | Narrow side |
| 8 | Long side portion |
| 9 | Corner |
| 9a, 9b | Inner surface |
| 10 | First clamping jaw |
| 21 | Outside surface |
| 22 | Clamping surface |
| 23 | Recess |
| 23 | Gripping portion |
| 25 | First groove |
| 26 | Second groove |
| 30 | Protrusion |
| 31 | Lateral protrusion surface |
| 40 | Second clamping jaw |
| 41 | Outside surface |
| 42 | Clamping surface |
| 43 | Recess |
| 45 | First groove |
| 46 | Second groove |
| 50 | Protrusion |
| 51 | Lateral protrusion surface |
| 52 | Gap |
| 55, 56 | Aperture |
| 60, 61 | Through-hole |
| 63 | First screw |
| 64 | Second screw |
| 65, 66 | Screw head |
| 67, 68 | Screw pin |
| 69, 70 | Thread |
| 71, 72 | Nut |
| A, B | Longitudinal axes |
| C, D | Longitudinal axes |
| Z | Crossing point |
| F | Symmetry axis |

The invention claimed is:

1. A rod coupler comprising:
a first clamping jaw and a second jaw wherein each clamping jaw comprises an outside surface and a clamping surface, wherein each clamping surface provides a first and second groove, each first and second groove on the first and second jaw clamping surface running laterally from a different part of the outside surface of each clamping jaw and extending into the rod coupler;
central longitudinal axes of the first groove and the second groove on the first and second clamping jaw intersect at an angle ($\alpha$) that is equal to or less than 160°;
the first and second grooves are positioned on the first and second jaw clamping surfaces such that, when the first and second clamping jaws face one another with their clamping surfaces in locking position, the first and second groove of the first clamping jaw faces the first and second groove of the second clamping jaw, wherein opposing first and second grooves form a first and second aperture, wherein each of the first and second apertures extends laterally from the outside surface of the clamping jaws into the rod coupler and is adapted for receiving a rod;
wherein the first and second clamping jaws provide, in a locking position, first and second spaced through-holes extending from the outside surface of the first clamping jaw through the opposing clamping surface of the first and second jaws to the outside surface of the second clamping jaw, wherein first and second screws are received in the respective first and second through-holes for locking the clamping jaws; and
wherein the first clamping jaw comprises a recess extending from the outside surface towards the clamping surface of the first jaw, the recess located between the first and second spaced through holes and away from the central longitudinal axes, the recess defining a through-opening, wherein the through-opening abuts or extends through the first and second apertures such that a portion of a rod received in the first or second grooves may be visible through the recess, wherein the recess provides hand gripping portions, the hand gripping portions including smooth corners and tapered edges to facilitate the handling of the rod coupler.

2. The rod coupler according to claim 1, characterized in that said clamped rods are positively locked at least with respect to said angle ($\alpha$).

3. The rod coupler according to claim 1, wherein the first and second grooves merge into one another.

4. The rod coupler according to claim 3, wherein the first and second grooves cross one another at a crossing point.

5. The rod coupler according to claim 4, wherein each clamping jaw provides a corner that extends from the crossing point towards the opposing clamping jaw and forms part of a lateral wall of the groove.

6. The rod coupler according to claim 1, wherein the first and second grooves have different diameters or shapes for clamping rods of different diameters or shapes.

7. The rod coupler according to claim 1, wherein the first and second clamping jaw provides a protrusion on its clamping surface, wherein said protrusions provide a lateral protrusion surface, wherein the lateral protrusion surfaces of said the first and second clamping jaws act together as a stop against further relative rotation when said clamping jaws are in locking position.

8. The rod coupler according to claim 1, wherein said first and second clamping jaws provides three or four or more straight grooves on its clamping surface provided with their longitudinal axis at different angles with respect to one another and forming three or four or more grooves for receiving three or four or more rods when the clamping jaws are locked against one another.

9. The rod coupler according to claim 1, wherein said clamping jaws are identical clamping jaws and are provided as a single piece.

10. The rod coupler as set forth in claim 1 wherein the second jaw comprises a recess extending from the outside surface towards the clamping surface of the second jaw, the recess located between the first and second spaced through holes and away from the central longitudinal axes, wherein the recess provides hand gripping portions, the hand gripping portions facilitating the handling of the rod coupler.

11. A rod coupler comprising:
a first clamping jaw and a second clamping jaw;
wherein each first and second clamping jaw comprises an outside surface and a clamping surface;
wherein each clamping surface provides at least first and second straight grooves, each groove running laterally from a different part of the outside surface of a respective first and second clamping jaw extending into the rod coupler;
a central longitudinal axis of a first groove and of a second groove on each clamping surface intersects within the first and second jaw outside surface and include an angle that is equal to or less than 160°;
first and second bores of each clamping jaw for receiving first and second screws for locking the clamping surfaces of the first and second jaws against one another for clamping the rods;
wherein said first and second grooves are positioned on each clamping surface such that, when the first and second clamping jaws face one another with their clamping surfaces in a locking position, the first and the second groove of the first clamping jaw face, the first and second grooves of the second clamping jaw, wherein the facing grooves form an aperture, wherein each of the two apertures extends laterally from the outside surface of said clamping jaws into the rod coupler and is adapted for receiving a rod when the first and second screws are engaged in the first and second bores;
and
wherein the first clamping jaw comprises a recess extending from the outside surface towards the clamping surface located between the first and second bores and away from the central longitudinal axes, the recess defining a through-opening, wherein the through-opening abuts or extends through the two apertures such that a portion of a rod received in the first or second grooves may be visible through the recess, wherein the recess provides a hand gripping portion to facilitate holding the rod coupler.

12. The rod coupler according to claim 11, wherein the first screw is locked in the first bore by clockwise rotation for locking the clamping jaw clamping surfaces.

13. The rod coupler according to claim 11, wherein said recess form a through-opening through the rod coupler when the clamping jaw surfaces are locked against one another.

14. The rod coupler as set forth in claim 11 wherein the second jaw comprises a recess extending from the outside surface towards the clamping surface of the second jaw, the recess located between the first and second spaced through holes, wherein the recess provides hand gripping portions, the hand gripping portions facilitating the handling of the rod coupler.

15. A rod coupler comprising:
a first clamping jaw, a second clamping jaw, and locking screws for locking said clamping jaws against one another;
wherein each clamping jaw comprises an outside surface and a clamping surface;
wherein each clamping surface provides at least two straight grooves, each groove running laterally from a different part of the outside surface extending into the rod coupler;
a central longitudinal axis of a first groove and of a second groove of said at least two grooves on one clamping surface include an angle that is equal to or less than 160°;
wherein said grooves are positioned on the clamping surfaces such that, when the clamping jaws face one another with their clamping surfaces in locking position, at least the first and the second groove of the at least two grooves of the first clamping jaw face each a groove of the second clamping jaw, wherein opposing grooves form an aperture, wherein each of the at least two apertures extends laterally from the outside surface of said clamping jaws into the rod coupler and is adapted for receiving a rod when the locking means is released;
wherein the clamping jaws are locked by the locking screws for clamping the rods received in said apertures;
wherein the clamping jaws provide, in a locking position, spaced first and second bores that run from the outside surface of the first clamping jaw through the opposing clamping surfaces to the outside surface of the second clamping jaw and in that said locking screws comprise a first and second screw that are respectively received in the first and second bores for locking rods in the first and second grooves; and
wherein the clamping jaws provide in a locking position at least two or more through-holes that run straight from the outside surface of the first clamping jaw through the opposing clamping surfaces to the outside surface of the second clamping jaw, wherein, the first clamping jaw comprises a recess extending from the outside surface towards the clamping surface of the first jaw, the recess located between the spaced first and second bores and away from the central longitudinal axes, and the recess forming a hand gripping portion, the recess defining a through-opening, wherein the through-opening abuts or extends through the two apertures such that a portion of a rod received in the first or second grooves may be visible through the recess.

16. The rod coupler according to claim 15, wherein each clamping jaw provides a protrusion on its clamping surface, wherein said protrusions provide each a lateral protrusion surface, wherein the lateral protrusion surfaces of said clamping jaws act together as a stop against further relative rotation, preferably clockwise rotation.

17. The rod coupler as set forth in claim 15 wherein the second jaw comprises a recess extending from the outside surface towards the clamping surface of the second jaw, the recess located between the first and second spaced through holes, wherein the recess provides hand gripping portions, the hand gripping portions facilitating the handling of the rod coupler.

18. A rod coupler comprising:
a first clamping jaw, a second clamping jaw, and a first and second locking screw for locking said clamping jaws against one another, the first and second jaws comprising spaced first and second bores for receiving the first and second locking screws;
wherein the first and second clamping jaws comprise an outside surface, the first clamping jaw comprising a first clamping surface and the second clamping jaw comprising a second clamping surface, the first and second clamping surfaces facing one another in a clamping position;
wherein each first and second clamping surface comprises first and second straight grooves, each groove running laterally from a different part of the outside surface extending into and through the rod coupler, the first and second grooves on each of the first and second jaws intersecting within the outside surface of each jaw and extend through a respective first and second opening in the outside surface;
a first central longitudinal axis of the first groove and a second central longitudinal axis of the second groove on each clamping surface intersect within the first and second clamping jaws to form an angle ($\alpha$) that is equal to or less than 160°;
wherein the first and second grooves are positioned on the facing clamping surfaces such that, when the clamping jaws face one another with their clamping surfaces in the clamping position, the first and the second grooves of the first clamping jaw face the respective first and second grooves of the second clamping jaw to form first and second passageways adapted to receive a rod, wherein the first and second passageways are open to first and second apertures in the outside surface extending parallel to the longitudinal axes of the first and second grooves, wherein each of the first and second apertures extend laterally from the outside surface of said clamping jaws into the respective first and second passageways at a location on the outside surface spaced from the opening of the first and second grooves in the outside surface a distance sufficient to leave a portion of the outside surface of the first and second jaws located between the first and second openings in the outside surface and the respective first and second apertures;
wherein the clamping jaws are locked by the first and second locking screw for clamping the rods received in the grooves; and
wherein the first clamping jaw comprises a recess extending from the outside surface of the first jaw towards the first jaw clamping surface, the recess located between the spaced first and second bores of the first jaw member and away from the first and second central longitudinal axes, the recess capable of being used as a hand gripping portion of the clamping jaws, the recess defining a through-opening, wherein the through-opening abuts or extends through the first and second apertures such that a portion of a rod received in the first or second grooves may be visible through the recess.

19. The rod coupler as set forth in claim 18 wherein the second jaw comprises a recess extending from the outside surface towards the clamping surface of the second jaw, the recess located between the first and second spaced through holes, wherein the recess provides hand gripping portions, the hand gripping portions facilitating the handling of the rod coupler.

\* \* \* \* \*